US010098917B2

(12) United States Patent
Raykov et al.

(10) Patent No.: US 10,098,917 B2
(45) Date of Patent: *Oct. 16, 2018

(54) PAROVIRUS HAVING A CPG-ENRICHED GENOME USEFUL FOR CANCER THERAPY

(71) Applicants: Deutsches Krebsforschungszentrum Stiftung Des Oeffentlichen Rechts, Heidelberg (DE); Ruprecht-Karls-Universitaet Heidelberg, Heidelberg (DE)

(72) Inventors: Zahari Raykov, Heidelberg (DE); Jean Rommelaere, Heidelberg (DE); Nathalia Giese, Schriesheim (DE); Marc Aprahamian, Heidelberg (DE)

(73) Assignees: Deutsches Krebsforschungszentrum Stiftung des oeffentlichen Rechts, Heidelberg (DE); Ruprecht-Karls-Universiaet Heidelberg, Heidelberg (DE)

( * ) Notice: Subject to any disclaimer, the term of this patent is extended or adjusted under 35 U.S.C. 154(b) by 209 days.

This patent is subject to a terminal disclaimer.

(21) Appl. No.: 13/887,029

(22) Filed: May 3, 2013

(65) Prior Publication Data
US 2013/0344034 A1    Dec. 26, 2013

Related U.S. Application Data

(63) Continuation of application No. 12/810,410, filed as application No. PCT/EP2008/010972 on Dec. 19, 2008, now Pat. No. 8,535,929.

(30) Foreign Application Priority Data

Dec. 28, 2007  (EP) .................................... 07025215

(51) Int. Cl.
A61K 35/768    (2015.01)
C12N 7/00      (2006.01)
A61K 39/00     (2006.01)

(52) U.S. Cl.
CPC .............. *A61K 35/768* (2013.01); *C12N 7/00* (2013.01); *A61K 2039/55561* (2013.01); *C12N 2750/14321* (2013.01); *C12N 2750/14332* (2013.01)

(58) Field of Classification Search
CPC ........ A61K 35/768; A61K 2039/55561; C12N 7/00
See application file for complete search history.

(56) References Cited

U.S. PATENT DOCUMENTS

2004/0186067 A1*  9/2004  Krieg et al. ................. 514/44
2004/0220124 A1* 11/2004  Rommelaere et al. ....... 514/44

OTHER PUBLICATIONS

Moehler et al (Hum Gene Ther. 2005, 16(8):996-1005.*
Schneeberger et al (Journal of Investigative Dermatology (2004) 123, 371-379.*
Dale et al (Vaccine 23 (2004) 188-197.*
Meng et al Int. J. Cancer: 116, 992-997, 2005).*
Sivori et al (Eur J Immunol 2006; 36:961-967.*
Kestler et al., Human Gene Therapy, 1999, 10: 1619-1632.*
Raykov et al Int. J. Cancer: 109, 742-749 (2004).*
Rommelaere et al, Cytokine Growth Factor Rev., 2010, vol. 21, p. 185-195.*
Grekova et al Cancer Biol Ther. Nov. 15, 2011; 12(10):888-95.*
Li and Rhode (Virology 194, 10-19 (1993.*
Fred Gage Nature, 392: 18-24, 1998.*
Spranger (Kidney International (2008) 74, 14-21.*
Jaffee et al (Methods, 1997, 12(2), 143-153.*
Srivatsan et al (Hum Vaccine Immunother. Jan. 1, 2014; 10(1): 52-63.*
Voskoglou-Nomikos et al (Clinical Cancer Research, 2003, 9, 4227-4239.*
Ochsenbein et al Proc. Natl. Acad. Science, 1999, 96, 2233-2238.*
Zipris et al J Immunol 2007; 178:693-701.*
Kowalczyk et al Acta Biochimica Polonica, 2003, 613-624.*
Raykov Zahari et al, "Arming parvoviruses with CpG motifs to improve their oncosuppressive capacity", International Journal of Cancer, vol. 122, No. 12, Jun. 15, 2008, pp. 2880-2884 XP002484045.
Schneeberger A et al, "CpG motifs are efficient adjuvants for DNA cancer vaccines", Journal of Investigative Dermatology, vol. 123, Jan. 1, 2004, pp. 371-379 XP003009181.
Moehler Markus H et al, "Parvovirus H-1-induced tumor cell death enhances human immune response in vitro via increased phagocytosis, maturation, and cross-presentation by dendritic cells", Human Gene Therapy, vol. 16, No. 8, Aug. 2005, pp. 996-1005 XP 002484046.
Raykov Zahari et al, "Combined oncolytic and vaccination activities of parvovirus H-1 in a metastatic tumor model", Oncology Reports, vol. 17, No. 6, Jun. 2007, pp. 1493-1499 XP 002484047.
International Search Report and PCT/ISA/237 dated May 28, 2009 (Eight (8) pages).
Schneeberger et al., Journal of Investigative Dermatology, 2004, 123, pp. 371-379.
Sivori et al., Eur J. Immunol 2006, 36: 961-967.
Moehler et al., Hum Gene Ther. 2005, 16(8): 996-1005, I.
Dale et al., Vaccine 23, 2004, 188-197.

(Continued)

Primary Examiner — Anoop K Singh
(74) Attorney, Agent, or Firm — Crowell & Moring LLP

(57) ABSTRACT

A parvovirus characterized by a CpG-enriched genome, wherein the genome contains at least 2 additional CpG inserts that are not present in the wild type genome is described as well as the use of said parvovirus, e.g., a parvovirus based on parvovirus H1, LuIII, Mouse minute virus (MMV), Mouse parvovirus (MPV), Rat minute virus (RMV), Rat parvovirus (RPV), Rat virus (RV), vectors based on the foregoing viral species, and/or cells capable of actively producing the foregoing viral species for the preparation of a pharmaceutical composition, e.g., for the treatment of cancer, preferably pancreas carcinoma, hepatoma or lymphoma.

3 Claims, 3 Drawing Sheets

Specification includes a Sequence Listing.

(56) References Cited

OTHER PUBLICATIONS

Meng et al., Int. J. Cancer: 116, 992-997, 2005.
Xu Li et al., "The Parvovirus H-1 NS2 Protein Affects Viral Gene Expression through Sequences in the 3' Untranslated Region", Virology 194, 10-19 (1993).
Satoshi Uematsu, "Toll-like Receptors and Type I Interferons", Journal of Biological Chemistry, May 25, 2007, vol. 282, No. 21, 15319-15323.

* cited by examiner

SEQUENCE LISTING

<160> NUMBER OF SEQ ID NOS: 7

<210> SEQ ID NO 1
<211> LENGTH: 96
<212> TYPE: DNA
<213> ORGANISM: Parvovirus H1

<400> SEQUENCE: 1
gttaacgttt acagctgact agtcgtttgc tcagtctaac gttcttgtct attgtcgttt       60
actagtctct taacgtttca tctacttgtc gttaac                                 96

<210> SEQ ID NO 2
<211> LENGTH: 25
<212> TYPE: DNA
<213> ORGANISM: artificial sequence
<220> FEATURE:
<223> OTHER INFORMATION: primer

<400> SEQUENCE: 2
atctggagga actggcaaaa ggacg                                             25

<210> SEQ ID NO 3
<211> LENGTH: 25
<212> TYPE: DNA
<213> ORGANISM: artificial sequence
<220> FEATURE:
<223> OTHER INFORMATION: primer

<400> SEQUENCE: 3
ccttaggcta gattctggtg acagc                                             25

<210> SEQ ID NO 4
<211> LENGTH: 22
<212> TYPE: DNA
<213> ORGANISM: artificial sequence
<220> FEATURE:
<223> OTHER INFORMATION: primer

<400> SEQUENCE: 4
ggcattgctg tcctgtgatt ac                                                22

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
actcagttat gttgggggta gg                                                22

<210> SEQ ID NO 6
<211> LENGTH: 23
<212> TYPE: DNA
<213> ORGANISM: artificial sequence
<220> FEATURE:
<223> OTHER INFORMATION: primer

<400> SEQUENCE: 6
gctcgtagta ttttggcagg acc                                               23

<210> SEQ ID NO 7
<211> LENGTH: 23
<212> TYPE: DNA
<213> ORGANISM: artificial sequence

```
<220> FEATURE:
<223> OTHER INFORMATION: primer

<400> SEQUENCE: 7
cgggtatcct tgcttagatg agc                                          23
```

PAROVIRUS HAVING A CPG-ENRICHED GENOME USEFUL FOR CANCER THERAPY

This application is a continuation of application Ser. No. 12/810,410, filed Jun. 24, 2010, which is a national stage of PCT International Application No. PCT/EP2008/010972, filed Dec. 19, 2008, which claims priority under 35 U.S.C. § 119 to European patent application 07025215.0, filed Dec. 28, 2007, the entire disclosure of which is herein expressly incorporated by reference.

The present invention relates to a parvovirus characterized by a CpG-enriched genome, wherein the genome contains at least two additional CpG motifs that are not present in the wild type genome. The present invention also relates to the use of said parvovirus for cancer therapy.

Oncolytic viruses such as rodent parvoviuses represent novel tools for cancer treatment. Besides specifically killing cancer cells (oncolysis), these agents also provide danger signals prompting the immune system to eliminate virus-infected tumours. As a consequence of oncolytic events, the innate and adaptive immune systems gain access to tumour antigens, which results in cross-priming and vaccination effects. Rodent parvoviruses are single-stranded DNA viruses possessing "intrinsic" oncolytic activity, i.e. they preferentially replicate in and kill cancer cells of both murine and human origin (1). Yet the anticancer efficacy of the most promising candidates for human clinical applications (including H-1PV) needs to be improved.

Therefore, it is the object of the present invention to provide improved parvoviruses for therapeutic uses.

According to the invention this is achieved by the subject matters defined in the claims. The present invention is based on the applicant's findings that improved oncolytic viruses can be generated by combining the beneficial features of oncolysis and vaccination. An oncolytic parvovirus vector was designed with extra CpG motifs in its genome causing them to accumulate selectively in tumour cells through amplification of the viral genome, i.e., CpG-motif-containing derivatives of H-1PV were engineered and compared with the parental virus regarding their ability to enhance the efficacy of an autologous antitumour vaccine in an established rat model of hepatoma lung metastasis (2). Two CpG-enriched H-1PV variants (JabCG1 and JabCG2), preserving both the replication competence and the oncolytic features of the parental virus were engineered. The viruses were inoculated ex vivo into the vaccine prior to its subcutaneous injection into tumour-bearing animals. These are conditions where H-1PV fails to exert any significant direct oncolytic effect on metastases and essentially acts as an adjuvant by modulating how effectively the vaccine triggers an antitumour immune response (3). In keeping with their increased CpG content, the JabCG1 and JabCG2 genomes proved in vitro to be more potent triggers of TLR-9-mediated signalling than wild-type H-1PV DNA. Antitumour activity was evaluated in a rat model of MH3924A hepatoma lung metastases, where parental and modified viruses were inoculated ex vivo as adjuvants of a subcutaneously administered autologous vaccine. In this setup, which excludes direct oncolytic effects on metastases, the JabCG2 vector displayed enhanced immunogenicity, inducing markers of cellular immunity (IFN-γ) and dendritic cell activation (CD80, CD86) in mediastinal (tumour-draining) lymph nodes. This led to a significantly reduced metastatic rate (50%) as compared to other vaccination schedules (H-1PV-, JabCG1-, JabGC-, or mock-treated cells). The CpG motifs can be added to the H-1PV genome without impairing the ability of the virus to replicate and lyse tumour cells. Most interestingly, the addition of the CpG motifs can improve the capacity of parvoviruses, e.g., H-1PV, to turn infected tumor cells into a vaccine causing immune stimulation and suppression of metastases under conditions where the wild-type virus has little effect. This is the first demonstration that virus-induced oncosuppression can be enhanced by modifying the number of activator CpG motifs in the viral genome resulting in immunostimulation in vivo.

In summary, the present data provide evidence that increasing the number of immunostimulatory CpG motifs within oncolytic viruses makes it possible to improve their overall anticancer effect by inducing antitumour vaccination. The fact that parvoviruses selectively replicate in neoplastic cells should restrict CpG motif amplification to the tumor site, thereby minimising the risk of side effects.

(B) Southern blot analysis of viral DNA extracted from NBK cells 48 h after infection (at a multiplicity of 1 replication unit per cell) with the different CpG viruses (JabCG1, JabCG2, JabGC) or wild type H-1PV serving as a reference. The positions of viral single-stranded DNA (ss), monomer (mRF) and dimer (dab⁻) replicative forms are indicated.

(C) Cell survival measured using the MIT assay and expressed as percentage of living cells in virus- vs mock-treated cultures. NBK cells (seeded in a 96-well plate at $2\times10^3$ cells/well) were analysed 72h after inoculation of H-1PV or CpG-modified viruses at indicated multiplicities of infection (MOI). Values shown are means from measurements performed in quadruplicates.

(D) Methylation status of viral DNA extracted from NBK cells 48 h after infection (MOI 1) either with JabCG2 or H-1PV. After purification, the viral DNA was subjected (or not) to treatment with the indicated restriction enzymes. The presence of the viral replicative forms and the shifts in their size after digestion are marked with arrows. Results are representative of three experiments.

Figure 2:
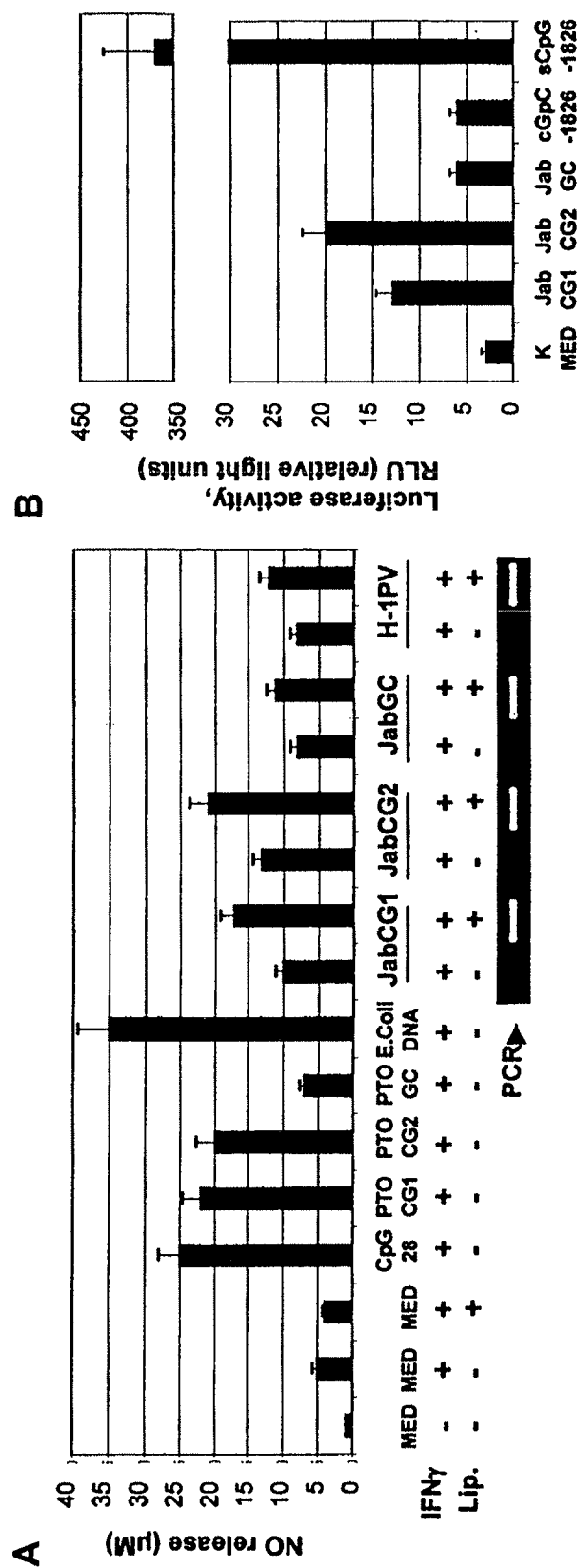

FIG. 2: TLR9-dependent activation of macrophages and HEKTLR9 cells by wild type and modified H-1PV DNAs (A) NO release from RAW 264.7 macrophages. The cells ($1\times10^5$ per well in a 96-well plate) were pre-activated overnight with recombinant IFN-γ (10 U/ml) prior to stimulation with the indicated oligonucleotides (CpG-28, PTOCG1, PTOCG2 and PTOGC) (5 µg/ml) or viral ssDNAs (JabCG1, JabCG2, JabGC, H-1PV) (5 µg/ml); E. coli DNA at the same concentration served as the positive control. RAW cells treated with medium (MED) supplemented (or not) with IFN-γ or Lipofectamine were included as negative controls. NO levels were determined at 18 hours using the Greiss reaction. Some of the ssDNA samples were preincubated with Lipofectamine™2000 (Lip; 1 µg/well) before application onto the cells. The ssDNA taken up by the RAW264.7 cells was detected by PCR 18h post treatment using a set of primers common for both H-1PV and CpG-modified genomes.

(B) TLR9-dependent signalling in viral DNA-treated cells. HEK cells stably expressing mTLR9 and containing a NFxB-driven firefly luciferase reporter gene, were seeded in 96 well plates ($2\times10^3$ cells per well) and stimulated with the indicated ssDNAs (JabCG1, JabCG2, JabCG, 10 µg/ml). The treatment with cGpCODN-1826 and sCpGODN-1826 oligonucleotides (5 µg/ml) served as a negative and positive control, respectively. At 6 h post treatment, TLR9-mediated induction of NFxB was assessed by measuring luciferase activity in cell lysates. Results shown are average values from 3 independent experiments.

Figure 3:
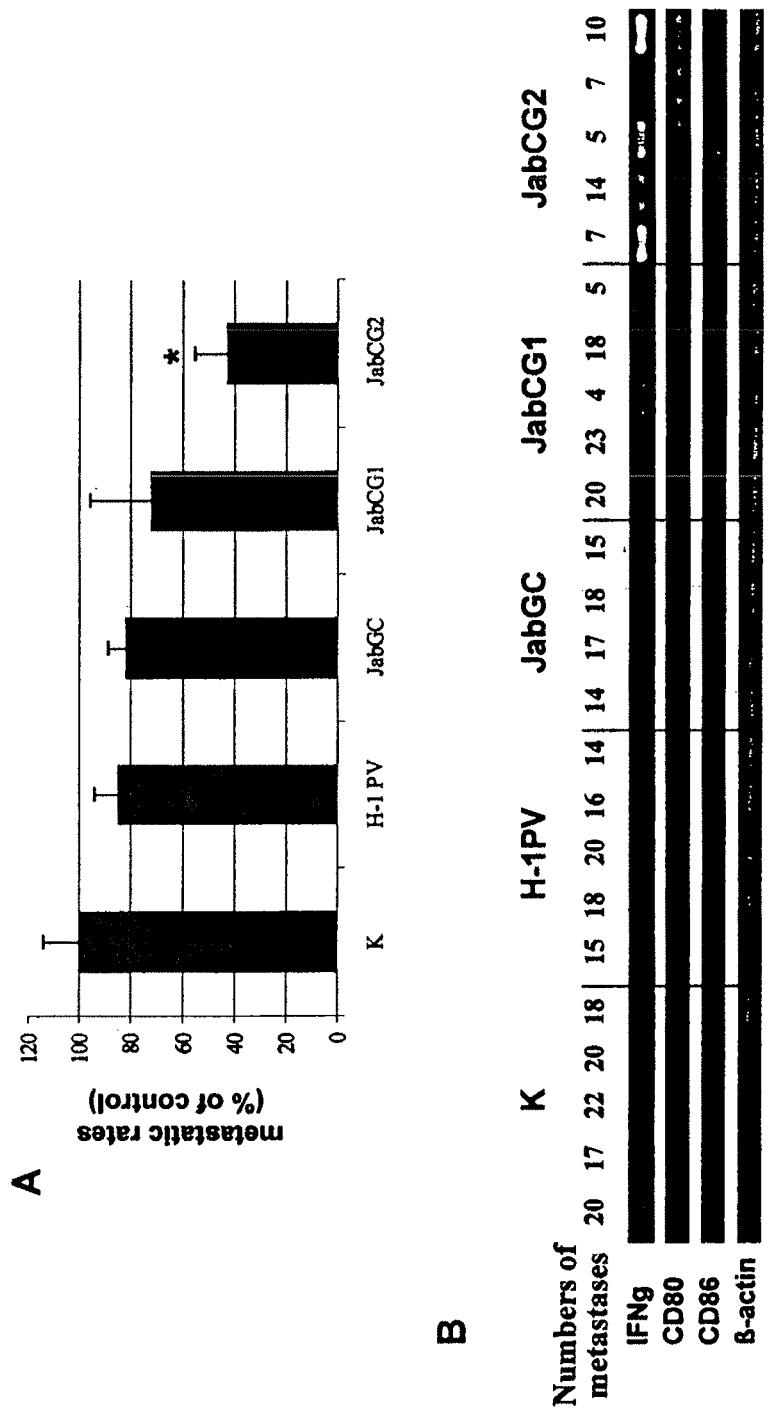

FIG. 3: In vivo anticancer potential of CpG-modified viruses (A) Rates of lung metastases in rats injected i.v. with MH3924A tumor cells at day 0, vaccinated s.c. with H-1PV or Jab vector-infected and irradiated autologous cells at day 10, and analyzed at day 30. Significant differences (p<0.05) relative to nontreated animals are indicated with asterisk.

(B) RT-PCR detection of immunological marker expression in mediastinal lymph nodes from above groups of animals. Data from individual rats are shown, with the corresponding numbers of metastases (over 2 mm in diameter) given on top of lanes. The samples were matched using β-actin as a reference.

Thus, the present invention provides a parvovirus (and a parvovirus-based vector) characterized by a CpG motif-enriched genome, wherein the genome contains at least one CpG motif that is not present in the wild type genome.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for producing said parvoviruses are readily determinable within the skill of the art based on the disclosure herein, without undue empirical effort.

The term "CpG motif" means an oligonucleotide containing or consisting of the dimer 5'-CG-3', which is, preferably, DNA.

The term "wherein the genome contains at least . . . additional CpG motifs that are not present in the wild type genome" relates to a genome of the parvovirus containing the additional CpG motifs in such a way that (a) the parvovirus retains its capacity to multiply and spread in neoplastic cells and (b) its competence for oncolysis and/or cytopathogenicity is not impaired.

Based on the instructions given in the Examples below the person skilled in the art can determine (a) suitable sites for insertion of CpG motifs and (b) the optimum number of CpG motifs which result in an enhanced adjuvant and therapeutic effect.

The preferred distance between individual CpG motifs is in the range of 1 to 200 nt.

In a preferred embodiment of the present invention, the parvovirus contains additional CpG motifs that are not present in the wild type genome in the range of 2 to 30, more preferably 6 to 12. In a particularly preferred embodiment, the parvovirus contains 6 additional CpG motifs that are not present in the wild type genome.

In another preferred embodiment of the invention, the additional CpG motifs are inserted into an intron or an untranslated 3'region of a gene. Based on the known nucleotide sequences of the genomes of various parvoviruses that are useful for the purposes of the present invention the person skilled in the art can easily determine suitable sites for insertion of the CpG motifs. Moreover, insertion of CpG motifs can be carried out by standard procedures, e.g., site-directed mutagenesis etc.

In a more preferred embodiment of the parvovirus of the present invention, the CpG motifs are inserted into the untranslated region at the 3'end of the VP transcription unit. Alternatively, the enrichment of the parvovirus genome with CpG motifs can be done by alternative codon usage. For example, the codon AGA (coding for arginine) could be replaced by the codons CGA, CGT, CGG or CGC and for the amino acid sequence Asp-Val the codons AAC-GTT could be used.

In a further more preferred embodiment of the parvovirus of the present invention, the CpG motifs comprise the nucleotide sequence AACGTT or GTCGTT.

In a particularly preferred embodiment, the parvovirus of the invention contains three AACGTT motifs and three GTCGTT motifs within the untranslated region at the 3'end of the VP transcription unit.

In one of the most preferred embodiments, the parvovirus of the invention is based on H-1PV (i.e. derived from H-1PV) and contains the nucleotide sequence SEQ ID NO: 1 5'-GTT AAC GTT TAC AGC TGA CTA GTC TGC TCAG TCT AAC GTT CTT GTCT AIT GTC GTT TAC TAG TCT CTT AAC GTT TCAT CTA CTT GTC GTT AAC-3' within the untranslated region at the 3'end of the VP transcription unit.

Particular useful parvoviruses are parvovirus H1 (H-1PV) or a related rodent parvovirus such as LuIII, Mouse minute virus (MMV), Mouse parvovirus (MPV), Rat minute virus (RMV), Rat parvovirus (RPV) or Rat virus (RV).

The present invention also provides a pharmaceutical composition containing a parvovirus of the invention or a cell producing said parvovirus (parvotherapeutic agent), e.g. human 293(T), NBK or rat RG2.

For administration, the parvotherapeutic agent can be combined with suitable pharmaceutical carriers. Suitable pharmaceutical carriers of a type well known in the art and readily commercially available, include phosphate buffered saline (PBS) solutions, water, emulsions such as oil/water emulsions, wetting agents of various types, sterile solutions, etc. Such carriers can be formulated with the parvotherapeutic agent(s) by conventional formulating methods for administration to the subject at a suitable dose.

Additional pharmaceutically compatible carriers can include gels, biosorbable matrix materials, implantation elements containing the therapeutic agent, or any other suitable vehicle, delivery or dispensing means or material(s).

Patients treatable by the parvotherapeutic agents of the invention include humans as well as non-human animals. Examples of the latter include, without limitation, animals such as cows, sheep, pigs, horses, dogs, and cats.

Administration of the parvotherapeutic pharmaceutical compositions to a patient, e.g. a brain tumor patient, may be effected in any of numerous suitable ways, e.g., by intravenous, intraperetoneal, subcutaneous, intramuscular, topical, intradermal, intracranial, and intratumoral administration. The route of administration, of course, depends on the nature of the disease and the specific therapeutic agent(s) contained in the pharmaceutical composition.

If such parvotherapeutic agent(s) comprise infectious virus particles with the ability to penetrate through the blood-brain barrier, treatment can be performed or at least initiated by intravenous injection of the viral therapeutic agent, e.g., H1-PV.

Since long-term intravenous treatment is susceptible to becoming inefficient as a result of the formation of neutralizing antibodies to the viral therapeutic agent, different modes of administration can be adopted after an initial regimen of intravenous viral administration, or such different administration techniques, e.g., intracranial or intratumoral virus administration, can be alternatively used throughout the entire course of parvoviral treatment.

As another specific administration technique, the parvotherapeutic agent (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus or derived vectors can also be injected, e.g., into a tumor, by stereotactic surgical techniques or by neuronavigation targeting techniques.

Administration of the parvoviral agents or compositions can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvotherapeutic composition is from an implanted device constructed and arranged to dispense the parvotherapeutic agent to the desired locus, e.g., tumor. For example, wafers can be employed that have been impregnated with the parvotherapeutic composition, e.g., parvovirus H1, wherein the wafer is attached to the edges of the resection cavity at the conclusion of surgical tumor removal. Multiple wafers can be employed in such therapeutic intervention.

Cells that actively produce the parvotherapeutic agent, e.g., parvovirus H1, or H1 vectors, can be injected into the desired tissue, e.g., tumor, or into a tumoral cavity after tumor removal.

Combinations of two or more of the above-described administration modes can be employed in any suitable manner, e.g., concurrently, contemporaneously, or sequentially.

The dosage regimen of the parvotherapeutic agent is readily determinable within the skill of the art, by the attending physician based on patient data, observations and other clinical factors, including for example the patient's size, body surface area, age, sex, the particular virus, cell, etc. to be administered, the time and route of administration, the type of disease, e.g., tumor type and characteristics, general health of the patient, and other drugs or therapies to which the patient is being subjected.

Accordingly, the present invention also relates to the use of a parvovirus according to the present invention or a cell producing said parvovirus for the preparation of a pharmaceutical composition for the treatment of a tumor. A preferred tumor is pancreas carcinoma, hepatoma and lymphoma being expected to be particularly amenable to treatment with a parvotherapeutic agent of the present invention.

The below examples explain the invention in more detail.

EXAMPLE 1

Materials and Methods (A) Reagents

Restriction enzymes were purchased from New England Biolabs, Frankfurt, Germany. PCR primers and phosphorothioated oligonucleotides [CpG-28 (4), PTO-CG1, PTO-CG2, PTO-GC] were synthesised by MWG, Ebersberg, Germany. *E. coli* DNA, IFN-γ, together with stimulatory (sCpGODN-1826) (5), and control cGpCODN-1826 (with inverted GpC motifs) oligonucleotides were obtained from InvivoGen, France. Lipofectamine™ 2000 was purchased from Invitrogen, Karlsruhe, Germany. All other reagents were from Sigma, Deisenhofen, Germany.

(B) Cell Cultures Treatment and Assays

The human embryonic kidney cell line HEK-TLR9 stably expressing the mouse TLR-9 receptor was a kind gift from Dr. Stefan Bauer (Technical University, München, Germany) (6). HEK-TLR9, 293T and NBK fibroblast cell lines, as well as the macrophage RAW 264.7 cells (ATCC, Manassas, USA) were cultured in DMEM. The ACI rat hepatoma cell line MH2934A (2) was cultivated in RPMI. All media were obtained from Sigma and supplemented with FCS (10%), penicillin (100 units/ml), and streptomycin (10mg/ml).

The cytopathic effect of the different viral isolates was assessed on NBK cells using MTT (3-(4,5-dimethylthiazolyl-2)-2,5-diphenyltetrazolium bromide) cytotoxicity assay 72 hours post infection. MH2934A cell cultures were γ-irradiated at 15 Gy prior to injection. Both procedures were performed as previously described (2). The Greiss colour reaction was used to determine NO levels in RAW 264.7 macrophage culture supernatants, as reported (8). Luciferase was assayed as previously described (6). Lipofectamine™ 2000 transfection was carried out according to the manufacturer's instructions.

(C) Viruses and Viral DNA Analysis

The JabCG1, JabCG2, and JabGC vectors were constructed by inserting the HpaI-digested fragments depicted in FIG. 1A into the pSR19 vector- an infectious H-1PV molecular clone (8). Viral vectors were produced as described (8) by transfecting 293T cells with the respective plasmids, followed by infection of NBK cells and purification so as to contain less than 2.5 EU/ml endotoxin. Viruses were titred on NBK cells in an infectious centre assay. Hirt's extraction method was used to isolate viral DNA from either purified virions or infected NBK cells. Replicative viral DNA forms were digested and revealed by Southern blotting (9). The DpnI enzyme cuts only methylated (') DNA at the GA'TC sequence, with multiple potential sites along the H-1PV genome. The HpaII enzyme digests DNA at unmethylated C'CGG motifs, five of which are located at the right end of the viral genome (see FIG. 1A). The AclI enzyme cuts DNA only at unmethylated cytosines within the AAC'GTT sequence, which was inserted in three copies giving rise to JabCG2 (FIG. 1A). All restriction reactions were performed under the conditions recommended by manufacturer.

(D) RT-PCR

Total RNA was extracted from mediastinal lymph nodes of treated animals and reverse transcribed into cDNA, as previously described (2). The following primers were used to amplify rat cDNAs: for IFN-γ, [SEQ ID NO: 2]5'-ATCTGGAGGAACTGGCAAAAGGACG-3'-forward, [SEQ ID NO: 3] 5'-CCTTAGGCTAGATTCTGGTGACAGC-3'-reverse; for CD80, [SEQ ID NO: 4] 5'-GGCATTGCTGTCCTGTGATTAC-3'-forward, [SEQ ID NO: 5] 5'-ACTCAGTTATGTTGGGGGTAGG-3'-reverse); for CD86, [SEQ ID NO: 6] 5'-GCTCGTAGTATTTTGGCAGGACC-3'-forward, [SEQ ID NO: 7] 5'-CGGGTATCCTTGCTTAGATGAGC-3'-reverse. The sizes of the corresponding PCR products were 290 by (IFN-γ), 314 by (CD80), and 337 by (CD86) Primer sequences for β-actin and H-1PV PCRs have been previously published (2).

(E) Animals and Tumour Model

MH3924A cells were inoculated through the femoral vein of anaesthetised ACI rats ($1\times10^5$ cells/animal) to induce metastasis, as already described (2). Vaccination was carried out 10 days after metastasis induction. For that purpose, MH3924A cells were infected or not with the respective purified viruses. After extensive washing with PBS 24 hours post infection the cells were irradiated and injected subcutaneously ($1\times10^6$ cells/animal) to the rats. The animals were sacrificed 20 days post-vaccination. After opening of the thoracic cavity, the trachea was canulated with a syringe, and the lungs were insufflated with 5-6 ml of 2% Indian ink solution in 0.9% NaCl. The white metastatic nodules (size 1-2 mm) were visualized on the black background of the lung tissue, after submerging the lungs in Fekette solution (58% Ethanol, 3% Formadehyde, 0.04% glacial acetic acid). The nodules on the surface of the organ were counted using a magnifying lens. Mediastinal lymph-nodes were extirpated after resection of the lungs. All experiments were performed in compliance with European and local guidelines.

(F) Statistics

Means and standard deviations were calculated for cell survival, stimulation, and metastasis incidence. The statistical significance of differences in metastatic incidence among the treatment groups of animals was assessed by one-way analysis of variance, followed by a parametric Student's unpaired t-test. The difference between individual values was considered significant at $P<0.05$. Instat 2.00® Macintosh software (GraphPad Software, San Diego, Calif.) was used for the analysis.

EXAMPLE 2

Construction and In Vitro Properties of CpG-modified Viruses

Since replication competence is essential to enabling oncolytic viruses to spread in the target tumour through secondary rounds of infection, a CpG-enriched parvovirus retaining the capacity to multiply and spread in neoplastic cells was constructed. The H-1PV genome is rather small and encodes proteins with pivotal functions in the viral life cycle. Therefore, a stretch of CpG-containing DNA was inserted into an untranslated region at the 3' end of the VP transcription unit. As indicated in FIG. 1A, the sequences cloned into two H-IPV variants (JabCG1, JabCG2) contained different numbers of two types of CpG motif: AACGTT (a general immunostimulatory element, reported to be active in murine models) (4) and GTCGTT (a motif shown also to activate human cells) (10). A third construct Gab GC) had an inverted (GC) orientation within the motifs and served as control.

The genomes of the viruses produced after transfecting 293T cells with the constructs were sequenced. Upon passaging in both permissive cell lines and animals, the JabCG1 virus was found progressively to accumulate mutations in the inserted CpG motifs (data not shown). It was hypothesised that this drift might be due to the presence in JabCG1 of neighbouring ACGT motifs (FIG. 1A, boxed sequences) constituting binding sites for the Parvovirus Initiation Factor (PIF) (11). This might reduce the concentration of PIF available for binding to the left-end origin of the genome, where its essential function is performed, thus selecting for mutants which don't bind PIF in the insert. In keeping with this view, the JabCG2 and JabGC variants (lacking homology with PIF-binding sites) remained stable through multiple passages (data not shown).

Figure 1:
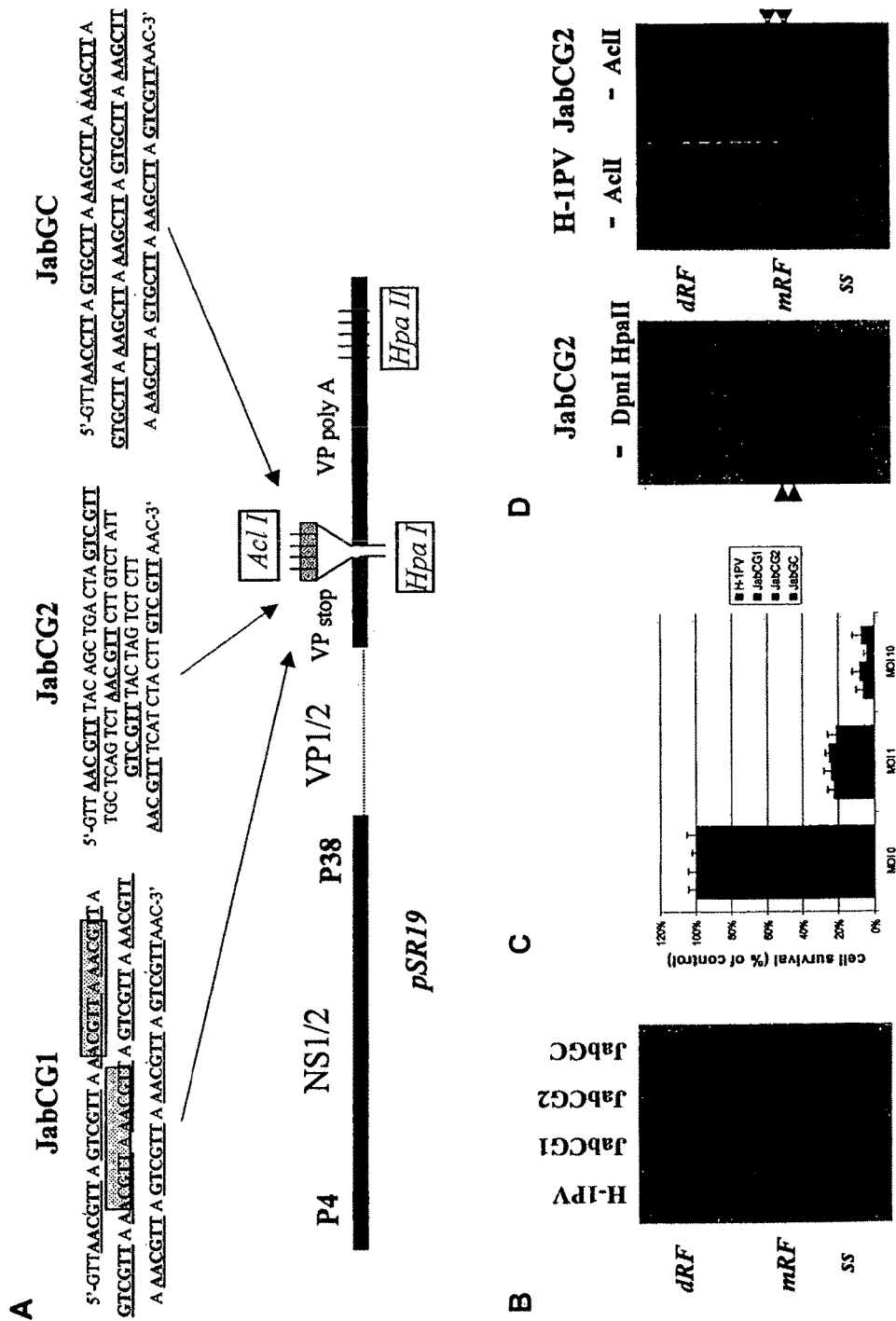
FIG. 1: Construction and in vitro properties of CpG-modified viruses (A) Sequences of CpG-containing fragments (with CpG motifs in bold) cloned at the HpaI site of the pSR19 vector. The H-IPV genome organisation is schematically represented with the locations of the capsid (VP1/2), and non-structural proteins (NS1/2) genes and their respective promoters (P4, P38). The positions of HpaII and AclI restriction sites are also indicated. Boxed sequences in JabCG1 represent the PIF-binding motifs.

When used in equivalent amounts (genome titres), the JabCG1/2 and JabGC mutants showed the same ability as the parental virus to replicate in and kill transformed NBK cells (FIG. 1 B, C). Thus, none of the insertions appeared to impair the competence of the virus for oncolysis and propagation. The methylation status of the viral DNA in infected cells was determined by restriction digestion with methylation-sensitive enzymes (RFLP analysis). Monomeric and dimeric viral replicative forms (FIG. 1D) were refractory to DpnI digestion. On the other hand, viral DNA was sensitive to HpaII and, in the case of the JabCG virus, to AclI, which recognises some specific sites confined to the CpG insert (AACGTT). Altogether, these results show that the viral DNA replication products, and in particular the cytosine residues present within the incorporated CpG motifs, were largely unmethylated—a prerequisite to triggering TLR-9 activation (5). In conclusion, the CpG motifs added to the H-1PV genome appeared not to impair viral replication or cytopathogenicity, and remained in the unmethylated form suitable for interaction with TLR9 receptors.

EXAMPLE 3

TLR9-Dependent Activation of Macrophages and HEKTLR9 Cells by Wild Type and Modified H-1PV DNAs Next the capacity of single-stranded DNA isolated from the different viruses to stimulate the release of nitrogen oxide from RAW 264.7 macrophages preactivated with IFN-γ was tested (7). The cells proved positive for TLR9 mRNA by RT-PCR (data not shown) and functionally responded to E. coli DNA (FIG. 2 A). NO release from RAW 264.7 cells incubated either with phosphorothioated oligonucleotides (PTO-CG1, PTO-CG2 and PTO-GC), with fragments identical to those used for cloning (see FIG. 1A), or with ssDNA isolated from the respective viruses (JabCG1, -CG2, -GC, or H-1PV) was measured. CpG-28 (a previously published activator oligonucleotide) (4) and E. coli DNA were used as positive controls. As shown in FIG. 2A, the added CpG motifs of the parvoviral DNA also displayed an activating capacity. The ssDNA of JabCG2 was more stimulatory than that of JabCG1, despite containing fewer CpG motifs (6 vs 13). This is consistent with the fact that these motifs got mutated during propagation of JabCG1. In keeping with earlier reports showing that transfection with a liposome-forming agent can enhance the stimulatory effect of microbial DNA through improved endosomal delivery (12), higher cellular uptake (as assessed by PCR) was achieved when Lipofectamine was used to transfect cells with the ssDNA of H-IPV or its CpG-enriched derivatives (FIG. 2B, lower panel). The release of NO from RAW 264.7 was correspondingly improved. To confirm that the ability of JabCG DNA to activate RAW 264.7 cells was due to recognition of the incorporated CpG motifs by TLR9, the stimulatory effects of the above-mentioned ssDNAs on HEK293 cells stably transfected with mouse TLR9 cDNA was measured. HEK293 cells do not normally express any TLRs, so TRL9 activation could be monitored through induction of the stably-integrated NF-kB-driven reporter gene (Luciferase). As shown in FIG. 2B, the JabCG1- and JabCG2-derived ssDNAs induced luciferase expression to a significantly higher level than JabGC-derived ssDNA, the negative control oligonucleotide (cGpC-1826), or medium. JabCG DNA, however, had a much lesser activating effect than the positive control oligonucleotide (sCpG-1826), most probably because it contains fewer CpG motifs per microgram DNA. From these data it can be concluded that H-1PV ssDNA has the capacity to trigger immune cell activation and that CpG-enrichment can enhance this effect via TLR9 activation.

EXAMPLE 4

Arming Parvoviruses with CpG Motifs Improves Their Oncosuppressive Capacity

Due to these results the impact of the inserted CpG motifs on the immunomodulatory and oncosuppressive activities of H-1PV in vivo was investigated. For this, an established rat lung hepatoma metastasis model, where the immunostimulatory capacity of parvoviruses can be assessed in the absence of any direct oncolytic effect on target tumours was chosen. The H-1PV-derived Jab mutants were tested for their adjuvant effects when administered with a vaccine consisting of X-ray-irradiated autologous (MH3924A) tumour cells providing only limited protection against metastases in the absence of infection. The virus was inoculated ex vivo into the vaccine prior to its irradiation and subcutaneous injection into metastasis-bearing rats. In this setup the viruses could clearly act only as vaccine adjuvants, since they were undetectable by RT-PCR in the lungs of treated rats and thus could not exert any direct oncolytic effect on lung metastases. As shown in FIG. 3A, the therapeutic effect of the cellular vaccine was improved only to a slight, barely significant extent when the adjuvant virus was H-1PV, JabGC, or JabCG1. This is in agreement with the lack or gradual loss of CpG motifs in these viruses. In contrast, the JabCG2-infected vaccine reduced the metastatic rate by over 50% as compared to non-treated controls. Besides showing a strikingly lower number of nodules above 2 mm in size, the group treated with the JabCG2 vaccine displayed no large necrotic nodules (exceeding 5 mm). In the other treatment groups, in contrast, this advanced stage of the disease was common. The expression of markers revealing activation of cellular immune response (IFN-γ) and maturation of dendritic cells (CD80, CD86) was measured by RT-PCR in mediastinal lymph nodes draining the lungs in which metastases were located. As illustrated in FIG. 3B, these innate and adaptive immune response indicators were strongly induced in the JabCG2-treated group, correlating with a favourable disease outcome. Most interestingly, the few animals that showed such marker elevation in the JabCG1 treatment group also had fewer metastases. Altogether these data strongly suggest that it is possible to reinforce the antitumour capacity of parvoviruses by arming them with CpG motifs that elicit enhanced immune activation. This is best exemplified by the JabCG2 virus, whose improved adjuvant and therapeutic effects clearly correlate with the preservation of inserted CpG motifs through multiple passages.

Parvoviral oncolysates of human melanomas have recently been shown to be stronger activators of dendritic cell maturation than freeze/thaw extracts (13). This effect was found to correlate with induction of HSP72 expression in the infected tumor cells. The present results show that this parvoviral immunostimulatory activity can be boosted by adding extra CpG motifs to the viral genome. This means that besides putative virus-induced cell factors, viral constituents contribute to immunomodulation. These constituents most likely include viral DNA species produced by infected tumor cells.

The small size of the H-1PV genome limits the number of CpG motifs that can be introduced into it without interfering with its packaging. It should be possible, nevertheless, to double the number of added activator CpG motifs, and perhaps to improve further the oncosuppressive capacity of H-1PV. This may be accomplished either by generating such motifs through alternative codon usage or by a viral intron located at the p38 promoter.

LIST OF REFERENCES

1. Rommelaere J, Giese N, Cziepluch C, Cornelis J J. Parvoviruses as anticancer agents. In: Sinkovics J G, Horvath J C, eds. Viral Therapy of Human Cancers. New York: Marcel Dekker; 2005. 627-75.
2. Raykov Z, Balboni G, Aprahamian M, Rommelaere J. Carrier cell-mediated delivery of oncolytic parvoviruses for targeting metastases. Int J Cancer 2004; 109:742-9.
3. Raykov Z, Grekova S, Galabov A S, Balboni G, Koch U, Aprahamian M, Rommelaere J. Combined oncolytic and vaccination activities of parvovirus H-1 in a metastatic tumor model. Oncol Rep 2007; 17:1493-9.
4. Meng Y, Carpentier A F, Chen L, Boisserie G, Simon J M, Mazeron J J, Delattre J Y. Successful combination of local CpG-ODN and radiotherapy in malignant glioma. Int J Cancer 2005; 116:992-7.
5. Krieg A M. Therapeutic potential of Toll-like receptor 9 activation. Nat Rev Drug Discov 2006; 5:471-84.
6. Fischer S F, Rehm M, Bauer A, Hofling F, Kirschnek S, Rutz M, Bauer S, Wagner H, Hacker G. Toll-like receptor 9 signaling can sensitize fibroblasts for apoptosis. Immunol Lett 2005; 97:115-22.
7. Lundberg P, Welander P, Han X, Cantin E. Herpes simplex virus type 1 DNA is immunostimulatory in vitro and in vivo. J Virol 2003; 77:11158-69.
8. Faisst S, Faisst S R, Dupressoir T, Plaza S, Pujol A, Jauniaux J C, Rhode S L, Rommelaere J. Isolation of a fully infectious variant of parvovirus H-1 supplanting the standard strain in human cells. J Virol 1995; 69:4538-43.
9. Russell S J, Brandenburger A, Flemming C L, Collins M K, Rommelaere J. Transformation-dependent expression of interleukin genes delivered by a recombinant parvovirus. J Virol 1992; 66:2821-8.
10. Sivori S, Carlomagno S, Moretta L, Moretta A. Comparison of different CpG oligodeoxynucleotide classes for their capability to stimulate human NK cells. Eur J Immunol 2006; 36:961-7.
11. Christensen J, Cotmore S F, Tattersall P. Parvovirus initiation factor PIF: a novel human DNA-binding factor which coordinately recognizes two ACGT motifs. J Virol 1997; 71:5733-41.
12. Dalpke A, Frank J, Peter M, Heeg K. Activation of toll-like receptor 9 by DNA from different bacterial species. Infect Immun 2006; 74:940-6.
13. Moehler MH, Zeidler M, Wilsberg V, Cornelis J J, Woelfel T, Rommelaere J, Galle P R, Heike M. Parvovirus H-1-induced tumor cell death enhances human immune response in vitro via increased phagocytosis, maturation, and cross-presentation by dendritic cells. Hum Gene Ther 2005; 16:996-1005.

The invention claimed is:

1. A replication-competent parvovirus comprising a CpG motif-enriched genome, wherein the parvovirus genome contains three AACGTT motifs and three GTCGTT motifs within the untranslated region at the 3' end of the VP transcription unit that are not present in the wild type genome, and wherein said parvovirus is parvovirus H1 (H-1 PV) and wherein the virus is stable through multiple passages.

2. A pharmaceutical composition containing the replication-competent parvovirus of claim 1.

3. A method of stimulating an immune response to treat a tumor in a patient in need thereof, said method comprising,
   (a) infecting autologous tumor cells with an effective amount of a replication-competent parvovirus comprising a CpG motif-enriched genome, wherein the genome contains the nucleotide sequence as set forth in SEQ ID NO: 1 within the untranslated region at the 3' end of the VP transcription unit, wherein said autologous tumor cells is pancreatic tumor cells or hepatoma cells;
   (b) irradiating said infected autologous tumor cells;
   (b) preparing a vaccine composition comprising the irradiated infected autologous tumor cells; and
   (c) subcutaneously administering to the patient in need thereof an effective amount of said vaccine comprising the irradiated infected autologous tumor cells that enhance innate and adaptive immune response, thereby treating tumor in said patient.

* * * * *